United States Patent [19]

Tokuyasu et al.

[11] Patent Number: 5,627,299
[45] Date of Patent: May 6, 1997

[54] PROCESS FOR PREPARING TRIBROMONEOPENTYL CHLOROALKYL PHOSPHATES

[75] Inventors: Noriaki Tokuyasu, Nara; Nobutaka Miyano, Aichi, both of Japan

[73] Assignee: Daihachi Chemical Industry Co., Ltd., Osaka, Japan

[21] Appl. No.: 616,601

[22] Filed: Mar. 15, 1996

[30] Foreign Application Priority Data

Mar. 29, 1995 [JP] Japan .................................. 7-071750
Jan. 9, 1996 [JP] Japan .................................. 8-001744

[51] Int. Cl.$^6$ .................................................. C07F 9/09
[52] U.S. Cl. ........................................ 558/91; 558/203
[58] Field of Search ............................. 558/91, 203

[56] References Cited

U.S. PATENT DOCUMENTS 4,046,719   9/1977   Stanaback et al. .
4,083,825   4/1978   Albright et al. .

FOREIGN PATENT DOCUMENTS 61-3797   2/1986   Japan .

*Primary Examiner*—Johann Richter
*Assistant Examiner*—Michael G. Ambrose
*Attorney, Agent, or Firm*—Greenblum & Bernstein P.L.C.

[57] ABSTRACT

A process of preparing tribromoneopentyl chloroalkyl phosphates comprising a first step of reacting phosphorus oxychloride with tribromoneopentyl alcohol and a second step of reacting the resultant formed in the first step with an alkylene oxide after a step of removing hydrochloric acid and unreacted phosphorus oxychloride present in the first reaction mixture to obtain a compound represented by the formula (1):

$$[(BrCH_2)_3C-CH_2O]_nP(OCHCH_2Cl)_{3-n}$$
$$\overset{O}{\underset{\|}{\phantom{P}}} \overset{R}{\underset{|}{\phantom{P}}}$$

, wherein R represents a hydrogen atom, or an alkyl or chloroalkyl group and n is from 0.95 to 1.15.

24 Claims, No Drawings

PROCESS FOR PREPARING TRIBROMONEOPENTYL CHLOROALKYL PHOSPHATES

BACKGROUND OF THE INVENTION

1. Field of the Invention

The present invention relates to a process for preparing tribromoneopentyl chloroalkyl phosphates. The tribromoneopentyl chloroalkyl phosphates can give flame retardancy and very low fogging property to polyurethane foam.

2. Description of Related Art

Polyurethane resin as a typical thermosetting resin is widely used in manufacture of various kinds of daily products including automobile parts because it can be obtained at a relatively low price and has remarkable characteristics such as good moldability. However, as polyurethane foam is combustible and tends to cause uncontrollable combustion once it catches fire, a lot of efforts have been made in this industry for flame-retarding of polyurethane foam. Today in some fields using polyurethane foam such as automobile interior furnishing, the flame-retardancy is legally required. Also, as environmental preservation is socially highlighted and dioxin (halodibenzodioxins) and CFC (chlorofluoro carbon) problems are zealously discussed, low fogging property in addition to the flame retardancy is a critical issue in auto-parts manufacture using polyurethane foam.

In order to give flame-retardancy to polyurethane foam, tribromoneopentyl chloroalkyl phosphates are conventionally added, which are disclosed in for example U.S. Pat. No. 4,046,719, U.S. Pat. No. 4,083,825 and Japanese Examined Patent Publication No. Sho61(1986)-3797. However, it has been found that the tribromoneopentyl chloroalkyl phosphate products as disclosed therein contain, in addition to the end flame-retardant tribromoneopentyl bis(chloroalkyl) phosphates, about 10 wt % tris(chloroalkyl)phosphate which is a monomeric component, about 20 wt % bis (tribromoneopentyl) chloroalkyl phosphate and about 5 wt % tris(tribromoneopentyl) phosphate which are crystalline components.

When a tribromoneopentyl chloroalkyl phosphate product is used as flame-retardant, it is desirable that the content of the monomeric component is as low as possible since it easily vaporizes by heat and thus adversely affects the fogging property.

It is also desirable that the content of the crystalline bis(tribromoneopentyl)chloroalkyl phosphate and tris (tribromoneopentyl)phosphate is as low as possible because they affect the viscosity of product, producing bad effects on the workability due to high viscosity and solidification.

Under these circumstances, there has been demand for a tribromoneopentyl chloroalkyl phosphate product exhibiting low fogging property with the lowest content of monomers and providing a low viscosity for good workability with the lowest content of crystalline components.

SUMMARY OF THE INVENTION

In order to eliminate the above-described drawbacks of the prior arts, it is an object of the present invention to provide a process of preparing tribromoneopentyl chloroalkyl phosphates with good workability which are capable of giving flame-retardancy and low fogging property to polyurethane foam.

Specifically, it is an object of the present invention to provide a process decreasing the contents of monomeric and crystalline components in the tribromoneopentyl chloroalkyl phosphate.

The inventors, after eager study on synthesis of tribromoneopentyl chloroalkyl phosphates, have found the following:

In the reaction of phosphorus oxychloride with tribromoneopentyl alcohol for synthesizing tribromoneopentyl chloroalkyl phosphates, tribromoneopentyl phosphorodichloridate, bis(tribromoneopentyl) phosphorochloridate and tris(tribromoneopentyl)phosphate are also generated because of three functional groups of phosphorus oxychloride. In addition, unreacted phosphorus oxychloride remains.

Since the generated tris(tribromoneopentyl)phosphate is crystalline and the bis(tribromoneopentyl) phosphorochloridate makes crystalline bis (tribromoneopentyl)chloroalkyl phosphate in the subsequent reaction with an alkylene oxide, they increase the viscosity of the product and impair the workability in the addition thereof to polymers as well as in the reaction with the alkylene oxide. Also the residual unreacted phosphorus oxychloride, when it remains in the product after the reaction with alkylene oxide, forms an ester of a low boiling point, resulting in debased fogging property.

The inventors, therefore, have found that the content of a monomer component represented by the formula (2):

, wherein R represents a hydrogen atom, or an alkyl or chloroalkyl group, in a tribromoneopentyl chloroalkyl phosphate product has been reduced to 5 wt % or below (about half as much as in the product by the conventional process), the fogging property thereby improving, and the contents of crystalline bis(tribromoneopentyl)chloroalkyl phosphate and tris(tribromoneopentyl)phosphate have been reduced to 15 wt % or below, the workability thereby improving, by dividing the reaction steps conventionally conducted in sequence for synthesizing a tribromoneopentyl chloroalkyl phosphate into the first reaction of phosphorus oxychloride with tribromoneopentyl alcohol and the second reaction of the obtained ester with an alkylene oxide, using an excess of phosphorus oxychloride in the first reaction and removing unreacted phosphorus oxychloride remaining in the first reaction mixture prior to the second reaction.

In other words, the invention provides a process of preparing a tribromoneopentyl chloroalkyl phosphate comprising a first step of reacting phosphorus oxychloride with tribromoneopentyl alcohol and a second step of reacting the resultant formed in the first step with an alkylene oxide after a step of removing hydrochloric acid and unreacted phosphorus oxychloride present in the first reaction mixture to obtain a compound represented by the formula (1):

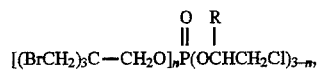

, wherein R represents a hydrogen atom, or an alkyl or chloroalkyl group and n is from 0.95 to 1.15.

Examples of the alkyl or chloroalkyl group of R in the above-described formula (1) are methyl, ethyl, propyl, isopropyl, butyl, sec-butyl, t-butyl, isopentyl, hexyl, 2-ethylhexyl, n-octyl, isooctyl and chloromethyl groups. Hydrogen and methyl group are especially preferred as R.

The reaction steps of the invention will be hereinafter described in detail.

The first step is to react phosphorus oxychloride with tribromoneopentyl alcohol at a molar ratio from 1.2 to 6.0:1.0, preferably at a molar ratio from 1.5 to 3.0:1.0 to obtain a phosphoric ester at a high purity which is an intermediate of the compound of the formula (1) and is represented by the formula (1'):

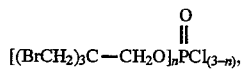

, wherein n is from 0.95 to 1.15.

When the phosphorus oxychloride is used in an amount of 1.2 moles or less to 1 mole of tribromoneopentyl alcohol, a large amount of tris(tribromoneopentyl)phosphate and bis (tribromoneopentyl)chloro phosphate are, formed, the former being crystalline and the latter becoming crystalline by the following reaction with the alkylene oxide, which results in a high viscosity or crystalline floats in the final product, and its workability is spoiled. When the phosphorus oxychloride is used in an amount over 6.0 moles to 1 mole of tribromoneopentyl alcohol, the production efficiency is disadvantageously lowered.

The reaction temperature is from about 50° to about 110° C., preferably from about 60° to about 80° C. Since the reaction does not fully proceed at a temperature below 50° C. and the intermediate decomposes at a temperature over 110°, a temperature out of the above-mentioned range is not desired.

The first step is preferably conducted in the presence of a Lewis acid catalyst, the examples thereof including magnesium chloride, aluminum chloride and titanium tetrachloride. Magnesium chloride, for example, is added in an amount of 2.5 to 35.0 millimoles, preferably 3.0 to 30.0 millimoles with respect to 1 mole of tribromoneopenthyl alcohol.

Subsequently, the generated hydrochloric acid and unreacted phosphorus oxychloride remaining in the reaction system are removed under reduced pressure at a temperature from about room temperature to an elevated temperature at which phosphoric esters exhibit heat resistance. Specifically, they can be efficiently removed using the thin-film distillation or nitrogen-topping method. The removal temperature is preferably from about 20° to about 110° C., more preferably from about 40° to about 100° C. since the intermediate phosphoric ester presents heat resistance up to about 120° C. The pressure is preferably reduced to the range from about 0.1 to about 500 torr.

If the step for removing phosphorus oxychloride is not taken, the remaining phosphorus oxychloride forms tris (chloroalkyl)phosphate contained in the final product, which has a bad influence as a main component of fogging substances. When the content of residual phosphorus oxychloride after the removal step does not exceed 4 to 6 wt % and preferably it does not exceed 2 wt %, good results can be obtained against fogging.

Next, by the second step of reacting the intermediate of the formula (1') with an alkylene oxide, the tribromoneopentyl chloroalkyl phosphate is almost continuously prepared.

Examples of the alkylene oxides used for the reaction include ethylene oxide, propylene oxide and butylene oxide, among which ethylene oxide and propylene oxide are preferred.

The theoretical usage amount of the alkylene oxide is calculated from the following formula:

$$\text{Theoretical usage amount of the alkylene oxide} = \frac{A \times B \times C}{100 \times 35.5},$$

wherein A represents weight(g) of the intermediate phosphoric ester, i.e., the reactant obtained in the first step, B represents content(%) of chlorine in the intermediate, C represents molecular weight of the alkylene oxide and 35.5 is atomic weight of chlorine.

The actual usage amount of the alkylene oxide is from the theoretical usage amount to 10 wt % excess thereof, preferably from 2 to 6 wt % excess of the theoretical usage amount. An excess of more than 6 wt % has an advantage in shortening the time required for completion of the reaction while having an economical disadvantage in increasing the usage amount of the alkylene oxide.

The reaction temperature is from about 40° to about 110° C., preferably from about 60° to about 90° C. A temperature below 40° C. is not practical because the progress of the reaction grows considerably slow at the temperature, and a temperature above 110° C. is not preferred because the intermediate decomposes at the temperature.

The second step can be efficiently conducted using a Lewis acid catalyst such as titanium tetrachloride and magnesium oxide. Titanium tetrachloride is added in an amount of about 2.3 to about 23.0 millimoles, preferably about 2.3 to about 11.5 millimoles to 1 mole of the intermediate.

The reaction time required for the completion of the reaction is, in an industrial scale, within the range from about 3 to about 5 hours when the raw materials are economically used. For example, when the reaction is conducted at a temperature within the range from 60 to 100° C. using 5 mol % excess of the alkylene oxide with respect to the intermediate, the time required for obtaining the product of good quality is from 2 to 4 hours.

The reaction mixture discharged from a reactor is formed into finished goods through washing and dehydrating steps. The washing can be conducted by a generally known method and both batch and continuous processes can be used. Specifically, the reaction mixture is washed with an aqueous solution of mineral acid such as sulfuric acid and hydrochloric acid, followed by an alkali or water cleaning and dehydration under reduced pressure. Alternatively, the reaction mixture is subjected to an alkali cleaning without being washed with the aqueous mineral acid solution, and, after removing by filtration or centrifugation the generated titanium compound (catalytic component) which is insoluble in water, is washed with water and dehydrated under reduced pressure.

The flame retardant for polyurethane foam obtained by the process of the present invention can be used, for example, as a composition of 0.1 to 60 parts by weight of tribromoneopentyl chloroalkyl phosphates represented by the formula (1) and, if necessary, 0 to 40 parts by weight of a non-reactive organophosphorous compound acting as a flame-retardant plasticizer, 0 to 50 parts by weight of a bromohydrin compound of pentaerythritol and 0 to 5 parts by weight of an antioxidant, with respect to 100 parts by weight of polyol which is a material of polyurethane.

The polyols are not specifically limited as long as they can be generally used for materials of polyurethane, but aptly used are polyols such as polyester polyol and polyether polyol which have about 2 to 8 hydroxyl groups per molecule and a molecular weight of about 250 to 6500. Polyols with a molecular weight of less than 250 are not suitable for forming urethane foam because of their great activity, and polyols with a molecular weight of more than 6500 damage workability because of their high viscosity.

Examples of polyols are diols; triols; and sorbitol, sucrose or polyols obtained by polymerization of ethylene oxide and/or propylene oxide with sorbitol, sucrose or ethylenediamine as an initiator. Specific examples are diols such as polyoxyethylene glycol and polyoxypropylene glycol; triols such as polyoxyethylene glycerol, polyoxypropylene glycerol, poly(oxyethylene)poly(oxypropylene) glycerol, polyoxyethyleneneohexanetriol, polyoxypropylenepentaneohexanetriol, poly(oxyethylene) poly(oxypropylene)neohexanetriol, poly(oxypropylene)1,2, 6-hexanetriol and polyoxypropylene alkanol; poly (oxyethylene)poly(oxypropylene)ethylenediamine; hexols such as polyoxyethylene sorbitol and polyoxypropylene sorbitol; octols such as polyoxyethylene sucrose and polyoxypropylene sucrose; and mixtures thereof. Also it is possible to use polyols, phosphorus-containing polyols or the like commercially available as special grades in which melamine or poly(ammonium phosphate) is dispersed. Preferred are polyether polyols of poly(oxyethylene/ oxypropylene)triols, with an average molecular weight ranging from about 250 to 6500.

The flame-retardant plasticizer preferably has an average molecular weight of 350 or more because it tends to fly by heat when it has a small molecular weight. Specific examples are tris(dichloropropyl)phosphate, Antiblaze 78 (chlorinated polyphosphonate manufactured by Albright & Wilson), Thermolin 101 [tetrakis(2-chloroethyl)ethylene diphosphate manufactured by Olin Urethane Chemicals], Phosgard XC20 [2,2 bis-(chloromethyl)-1,3-propanebis (chloroethyl)diphosphate manufactured by Monsanto Chemical Company], CR-30, CR-570 and CR-509 (halogen-containing phosphate phosphonate oligomer esters manufactured by Daihachi Chemical Industry Co., Ltd., CR-504 and CR-505 (halogen-containing diphosphate oligomer esters manufactured by Daihachi Chemical Industry Co., Ltd.), cresyl diphenyl phosphate and tricresyl phosphate.

The bromohydrin compounds of pentaerythritol are solid with the melting points, the specific examples thereof including dibromoneopentyl glycol and tribromoneopentyl alcohol. These can be liquefied by stirring with heat, and their liquid state can be retained after the temperature falls back to ordinary temperature.

Examples of the anti-oxidants include hydroquinone compounds represented by the formula (3):

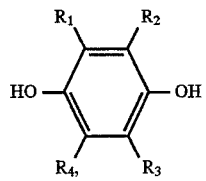

, wherein each of R1, R2, R3 and R4 represents a hydrogen atom or $C_{1-14}$ alkyl group, and/or trivalent organophosphorous compounds. Examples of the above-mentioned hydroquinones include hydroquinone, 2,5-di-t-amylhydroquinone, 2,5-dioctylhydroquinone, t-amylhydroquinone, t-butylhydroquinone and octylhydroquinone. Especially, hydroquinone compounds with excellent heat-resistance are 2,5-di-t-amylhydroquinone and 2,5-di-t-butylhydroquinone.

Examples of the above-mentioned trivalent organophosphorous compounds are triphenyl phosphite, tris (nonylphenyl)phosphite, diphenylisodecyl phosphite, tris(2, 4-di-t-butylphenyl)pentaerythritol diphosphite, tetrakis-(2, 4-di-t-butylphenyl)-4,4-diphenylene phosphonite.

An examplary method of producing polyurethane foam using the above-described composition will be described. That is, polyurethane foam is produced by adding the above composition to the reaction of the polyol and toluenediisocyanate (TDI) in the presence of a catalyst, water(or a blowing agent), a dispersant and the like, and then heating with stirring.

TDIs include isomers of 2,4- and 2,6-toluenediisocyanates and the concentration of these isomers preferably has the index ranging from about 80 to 120 in the 80/20 TDI ratio, but not limited thereto.

For the catalyst, tertiary amine catalysts (e.g., triethylenediamine, dimethylethanolamine and N-ethylmorpholine) can be used and for the blowing agent, compounds with low melting points such as water, fluorocarbon and methylene chloride can be used.

For the dispersant, nonionic surfactants such as ether-type, etherester-type and ester-type can be used. Specific examples are alkyl(methyl, ethyl, propyl, butyl, amyl, heptyl, octyl, nonyl, decyl, dodecyl, tridecyl) and aryl (phenyl, tolyl, xylyl, biphenyl, naphthyl)polyoxyethylene ether, alkyl aryl formaldehyde-condensed polyoxyethylene ether, polyoxyethylene ether of glycerin ester, polyethylene glycol fatty ester, propylene glycol ester, polyglycerin, sorbitan ester, fatty acid monoglyceride and mixtures thereof.

The present invention provides a tribromoneopentyl chloroalkyl phosphate product in which the crystalline components are contained only at a low percentage, thereby good workability being secured, and the monomer component is contained only at a low percentage, whereby generation of fogging being restrained, by dividing the reaction process for synthesizing the tribromoneopentyl chloroalkyl phosphate into the first reaction of phosphorus oxychloride with tribromoneopentyl alcohol, in which an excess of phosphorus oxychloride is used, and the second reaction of the obtained ester with alkylene oxide, prior to which unreacted phosphorus oxychloride remaining in the reaction mixture is removed. This method enables reduction of the monomer content to about 5 wt % or below (half of that in the conventional tribromoneopentyl chloroalkyl ;phosphate), thereby the fogging property is improved, and reduction to about 15 wt % or below of the contents of bis (tribromoneopentyl)chloroalkyl phosphate and tris (tribromoneopentyl)phosphate which are crystalline, thereby the workability is improved. In short, the invention provides a process of preparing a flame-retardant for polyurethane foam with good workability which is capable of giving fine retardancy, low-fogging property, high heat stability and scorch resistance.

By using such flame retardant excellent in flame retardancy, low-fogging property, heat stability and scorch resistance, it has become possible to provide products having good properties for automobile and furniture manufacturing.

The present invention will be further described with reference to the following examples; however, these examples are intended to illustrate the invention and are not to be construed to limit the scope thereof.

WORKING EXAMPLE 1

The First Step 307.0 g (2.0 moles) of phosphorus oxychloride, 324.7 g (1.0 mole) of tribromoneopentyl alcohol and 0.3 g (3.2 millimols) of magnesium chloride were filled in a one-liter four-necked flask provided with a stirrer, a thermometer and a condenser connected to a water scrubber, heated to 70° C. and allowed to react for 8 hours. After the reaction, the generated hydrochloric acid and unreacted phosphorus oxychloride were removed at a temperature of 70° C. at a vacuum degree of 5 tort in 2 hours, and then nitrogen was supplied at a flow rate of 5 m$^3$/hour at a vacuum degree of 20 torr for 2 hours. About 440 g of the intermediate phosphoric ester was obtained. The content of chlorine was 16.1%.

The Second Step 0.4 g (2.3 millimols) of titanium tetrachloride was added as a catalyst to the obtained intermediate and heated to 80° C. and 92.4 g (2.1 moles) of ethylene oxide was supplied in about 1 hour while maintaining the temperature. Then the temperature was raised to 90° C. and maintained for 1 hour.

After the reactant was alkali-cleaned with solution of soda ash (anhydrous sodium carbonate) and separated from the aqueous phase, about 503 g of the end phosphoric ester was obtained by collecting compounds of a low boiling point in vacuo.

The yield was calculated with respect to 100 for the entire tribromoneopentyl bis(chloroalkyl)phosphate theoretically expected to be synthesized from all the starting tribromoneopentyl alcohol.

From the area-ratio analysis of GPC (gel permeation chromatography), the generated product contained 95% tribromoneopentyl bis(chloroethyl)phosphate, 4% bis(tribromoneopentyl)chloroethyl phosphate and 1% tris(chloroethyl)phosphate.

WORKING EXAMPLE 2

The same procedure as in the example 1 was taken except that the hydrochloric acid and phosphorus oxychloride were removed through a distillation column at a temperature of 90° C. at a vacuum degree of 20 tort to obtain about 440 g of the intermediate phosphoric ester. The content of chlorine was 16.1%. 0.4 g (2.3 millimols) of titanium tetrachloride was added as a catalyst to the obtained intermediate and heated to 80° C. While maintaining the temperature, 121.8 g (2.1 moles) of propylene oxide was supplied in about 1 hour. Then the temperature was raised to 90° C. and maintained for 1 hour.

The reactant was after-treated as described in the example 1.

About 524 g of the end phosphoric ester was obtained.

From the area-ratio analysis of GPC, the generated product contained 95% tribromoneopentyl bis(chloropropyl) phosphate, 4% bis(tribromoneopentyl)chloropropyl phosphate and 1% tris(chloropropyl)phosphate.

WORKING EXAMPLE 3

The same procedure as in the example 1 was taken except that the amount of the starting phosphorus oxychloride was 230.5 g (1.5 moles) and the hydrochloric acid and the phosphorus oxychloride were removed through a distillation column at a temperature of 90° C. at a vacuum degree of 30 tort to obtain about 445 g of the intermediate phosphoric ester. The content of chlorine was 16.5%. 0.3 g (2.3 millimols) of titanium tetrachloride was added as a catalyst to the obtained intermediate and heated to 80° C. While maintaining the temperature, 126 g (2.2 moles) of propylene oxide was supplied in about 1 hour. Then the temperature was raised to 90° C. and maintained for 1 hour.

The reactant was after-treated as described in the example 1.

About 527 g of the end phosphoric ester was obtained.

From the area-ratio analysis of GPC, the obtained product contained 88% tribromoneopentyl bis(chloropropyl) phosphate, 8% bis(tribromoneopentyl)chloropropyl phosphate and 4% tris(chloropropyl)phosphate.

COMPARATIVE EXAMPLE 1

(Synthesis according to U.S. Pat. No. 4,046,719)

500 g (1.5 moles) of tribromoneopentyl alcohol and 0.8 g of magnesium oxide were filled in a flask, and heated to 60° C. Then 231.5 g (1.5 moles) of phosphorus oxychloride was added in 2 hours and the reactant was heated to 138° C. The temperature was maintained for 3 hours, while generated hydrocholoric acid was removed. About 674 g of the intermediate phosphoric ester was obtained and the content of chlorine was 16.2%. Next, after cooling to 95° C., 210.0 g (3.62 moles) of propylene oxide was added in 2.5 hours and then the temperature was maintained at 92° C. for 1 hour under reflux. The acid value was then 0.12.

Then the reactant was after-treated with sodium hydroxide and others to give 728 g of the product.

From the area-ratio analysis of GPC, the generated product contained 65% tribromoneopentyl bis(chloropropyl) phosphate, 20% bis(tribromoneopentyl)chloropropyl phosphate, 5% tris(tribromoneopentyl) phosphate and 10% tris(chloropropyl)phosphate.

COMPARATIVE EXAMPLE 2

The same procedure as in the comparative example 1 was taken for the synthesis except that 159.0 g (3.62 moles) of ethylene oxide was used instead of 210 g (;3.62 moles) of propylene oxide. The yield was 653 g.

From the area-ratio analysis of GPC, the generated product contained 61% tribromoneopentylbis(chloroethyl) phosphate, 22% bis(tribromoneopentyl)chloroethyl phosphate, 5% tris(tribromoneopentyl) phosphate and 12% tris(chloroethyl)phosphate.

COMPARATIVE EXAMPLE 3

307.0 g (2.0 moles) of phosphorus oxychloride, 324.7 g (1.0 mole) of tribromoneopentyl alcohol and 0.3 g (3.2 millimols) of magnesium chloride were filled in a flask, heated to 70° C. and allowed to react felt 6 hours. About 592 g of the intermediate phosphoric ester was obtained. The content of chlorine was 29.9%.

0.4 g (2.3 millimols) of titanium tetrachloride was added as a catalyst to the intermediate and heated to 80° C. Then, while the temperature was maintained, 230.0 g (5.23 moles) of ethylene oxide was added in 4 hours. After that, the same procedure as in the comparative example 1 was taken to give 677 g of the product.

From the area-ratio analysis of GPC, the generated product contained 55% tribromoneopentylbis(chloroethyl) phosphate, 3% bis(tribromoneopentyl)chloroethyl phosphate and 42% tris(chloroethyl)phosphate.

Table 1 shows the properties of the products:

TABLE 1

|  | Working Examples ||| Comparative Examples |||
|---|---|---|---|---|---|---|
|  | 1 | 2 | 3 | 1 | 2 | 3 |
| Material used |  |  |  |  |  |  |
| Phosphorus oxychloride (moles) | 2 | 2 | 1.5 | 1.5 | 1.5 | 2 |
| TBNA* (moles) | 1 | 1 | 1 | 1.5 | 1.5 | 1 |
| Kind of AO** (excessive phosphorus oxychloride) | EO (removed) | PO (removed) | PO (removed) | PO | EO | EO |
| Results Yields (g) | 503 | 524 | 527 | 728 | 653 | 677 |
| GPC Analysis*** |  |  |  |  |  |  |
| Compound A | 95 |  |  |  | 61 | 55 |
| Compound B |  | 95 | 88 | 65 |  |  |
| Compound C | 4 |  |  |  | 22 | 3 |
| Compound D |  | 4 | 8 | 20 |  |  |
| Compound E |  |  |  | 5 | 5 | 0 |
| Compound F | 1 |  |  |  | 12 | 42 |
| Compound G |  | 1 | 4 | 10 |  |  |
| Viscosity (cps) | 800 | 1700 | 2700 | 4500 | 10000 | 900 |
| State of liquid | Transp. liq. | Transp. liq. | Transp. liq. | Transp. liq. | Crystl. sus. | Transp. liq. |
| Workability | O | O | O | X | X | O |

Notes:
*TBNA: Tribromoneopentyl alcohol
**AO: Alkylene oxide
EO: Ethylene oxide
PO: Propylene oxide
***Compound A: Tribromoneopentyl bis(chloroethyl)phosphate
Compound B: Tribromoneopentyl bis(chloropropyl)phosphate
Compound C: Bis(tribromoneopentyl)chloroethyl phosphate
Compound D: Bis(tribromoneopentyl)chloropropyl phosphate
Compound E: Tris(tribromoneopentyl) phosphate
Compound F: Tris(chloroethyl)phosphate
Compound G: Tris(chloropropyl)phosphate In the "State of liquid" in Table 1, Tranp.liq. stands for transparent liquid and Crystl.sus. means that crystalline substances were suspended. In the "workability", O and X denote good and bad workability respectively.

Table 1 shows that the products of the invention are transparent liquids of lower viscosities containing less monomeric components and less crystalline components than those of the comparative examples.

Next, the flame-retardant compositions using the products obtained as described above were examined upon their flame-retardancy and fogging property.

Preparation of flame-retardant polyurethane foam of low fogging property:
Ingredients:
Polyol (polyether polyol manufactured by Mitsui Toatsu Chemicals, Inc., molecular weight:3000):100 parts
Isocyanate (tolylenediisocyanate manufactured by Mitsui Toatsu Chemicals, Inc., 42,4/2,6 80/20):59.5 parts
Silicone oil (trade name : F-242T, manufactured by Shin-Etsu Chemical Co., Ltd.):1.2 parts
Tin-base catalyst (trade name:STANN BL, manufactured by Sankyo Organic Chemicals Co., Ltd.):0.3 parts
Amine-base catalyst (trade name:Kaolizer NO.1, manufactured by Kao Corporation):0.1 parts
Water:4.5.parts
Methylene chloride:necessary parts
Flame-retardant:necessary parts Flexible urethane foam bodies were prepared according to the above recipe with the one-shot process.

Production of polyurethane foam

Polyol, silicone oil, catalysts, water and flame-retardant were blended in the amount (part by weight) as described in the above recipe and homogeneously mixed by stirring at 3000 r.p.m. for 1 minute. Then isocyanate was added and, after further stirring at 3000 r.p.m. for 5 to 7 seconds, the mixture was quickly poured to a cubic carton. Expansion was immediately observed and reached the maximum volume in several minutes. This was allowed to cure in an oven at 80° C. for 30 minutes. The obtained foam bodies had a flexible white cellular structure.

Samples were taken from the foam bodies obtained as described above for flammability test (flammability test MVSS-302). Also, for fogging test, deposit on glass was measured at 110° C. after 3 and 16 hours according to DIN 75201 (European fogging test).

As for properties, the density (kg/m$^3$)(Japanese Industrial Standard K-7222) and gas permeability (ml/cm$^2$/sec) (Japanese Industrial Standard L-1004, American Society for Testing and Materials D-737-46) were also measured.

Table 2 shows the results:

TABLE 2

| Density of Foam | Methylene 2 parts chloride MVSS-302 | | | Gas permeability: 100 Fogging | | Methylene 5 parts chloride MVSS-302 | | | Gas permeability: 100 Fogging | |
|---|---|---|---|---|---|---|---|---|---|---|
| | 30 kg/m3 Parts | Burning rate (cm/min) | Combustibility | After 3 hrs (mg) | After 16 hrs (mg) | 20 kg/m3 Parts | Burning rate (cm/min) | Combustibility | After 3 hrs (mg) | After 16 hrs (mg) |
| Working example 1 | 10 | 0.7 | NB | 0.3 O | 0.5 O | 15 | 0.6 | NB | 0.8 O | 1.0 O |
| Working example 2 | 10 | 0.8 | NB | 0.2 O | 0.3 O | 15 | 0.7 | NB | 0.5 O | 0.7 O |
| Working example 3 | 10 | 0.8 | NB | 0.5 O | 0.6 O | 15 | 0.7 | NB | 0.7 O | 0.9 O |
| Comparative example 1 | 10 | 0.8 | NB | 1.2 X | 1.6 X | 15 | 0.7 | NB | 1.5 X | 1.7 X |
| Comparative example 2 | 10 | 0.8 | NB | 1.5 X | 1.8 X | 15 | 0.7 | NB | 2.0 X | 2.5 X |
| Comparative example 3 | 10 | 1.1 | NB | 2.3 X | 4.5 X | 15 | 0.9 | NB | 3.8 X | 12.0 X |

NB: Non-burning

The symbols O and X in the "Fogging" in Table 2 denote good (low) and bad (high) fogging properties respectively.

Table 2 shows that the more monomers are contained, the worse the fogging properties are, though there is no significant difference among the burning rates.

The present invention provides the method for preparing a tribromoneopentyl chloroalkyl phosphate flame-retardant for polyurethane foam which enables reduction of the contents of the monomers and crystalline components in the synthesized tribromoneopentyl chloroalkyl phosphate securing low fogging property, high scorch-retardancy and good workability. The foam retains good properties without any closed cells and therefore with good gas permeability.

What is claimed is:

1. A process of preparing tribromoneopentyl chloroalkyl phosphates comprising:

reacting phosphorus oxychloride with tribromoneopentyl alcohol to obtain a first reaction mixture;

removing hydrochloric acid and unreacted phosphorus oxychloride present in the first reaction mixture to obtain a second reaction mixture; and reacting the second reaction mixture with alkylene oxide to obtain a compound represented by the formula (1):

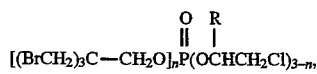

[(BrCH$_2$)$_3$C—CH$_2$O]$_n$P(OCHCH$_2$Cl)$_{3-n}$ wherein R represents a hydrogen atom, or an alkyl or chloroalkyl group and n is from 0.95 to 1.15.

2. The process according to claim 1 wherein in the reaction of phosphorus oxychloride with tribromoneopentyl alcohol the molar ratio of phosphorus oxychloride to tribromoneopentyl alcohol is from 1.2 to 6.0:1.0.

3. The process according to claim 1 wherein in the reaction of phosphorus oxychloride with tribromoneopentyl alcohol the molar ratio of phosphorus oxychloride to tribromoneopentyl alcohol is from 1.5 to 3.0:1.0.

4. The process according to claim 1 wherein the reaction of phosphorus oxychloride with tribromoneopentyl alcohol is conducted at a temperature within the range from about 50° to about 110° C.

5. The process according to claim 4 wherein the reaction of phosphorus oxychloride with tribromoneopentyl alcohol is conducted at a temperature within the range from about 60° to about 80° C.

6. The process according to claim 1 wherein the reaction of phosphorus oxychloride with tribromoneopentyl alcohol is conducted in the presence of a Lewis acid catalyst.

7. The process according to claim 6, wherein the Lewis acid catalyst is selected from the group consisting of magnesium chloride, aluminum chloride and titanium tetrachloride.

8. The process according to claim 7, wherein the Lewis acid catalyst is magnesium chloride.

9. The process according to claim 8, wherein the magnesium chloride is added in an amount of 2.5 to 35.0 millimoles with respect to 1 mole of tribromoneopentyl alcohol.

10. The process according to claim 9, wherein the magnesium chloride is added in an amount of 3.0 to 30.0 millimoles with respect to 1 mole of tribromoneopentyl alcohol.

11. The process according to claim 1 wherein the removal of hydrochloric acid and unreacted phosphorus oxychloride present in the first reaction mixture is conducted under reduced pressure at a temperature from room temperature to an elevated temperature at which the phosphoric esters exhibit heat resistance.

12. The process according to claim 1 wherein the removal of hydrochloric acid and unreacted phosphorus oxychloride present in the first reaction mixture is conducted under reduced pressure at a temperature from about 20° to about 110° C.

13. The process according to claim 1 wherein the removal of hydrochloric acid and unreacted phosphorus oxychloride present in the first reaction mixture is conducted under reduced pressure an a temperature from about 40° to about 100° C.

14. The process according to claim 1 wherein the phosphorus chloride does not exceed 6 wt % in said second reaction mixture.

15. The process according to claim 14 wherein the phosphorus oxychloride does not exceed 4 wt % in said second reaction mixture.

16. The process according to claim 1 wherein the alkylene oxide is ethylene oxide or propylene oxide.

17. The process according to claim 1 wherein the alkylene oxide is used in an amount within the range from a theoretical usage amount calculated from the following formula:

$$\text{Theoretical usage amount of the alkylene oxide} = \frac{A \times B \times C}{100 \times 35.5}$$

wherein A represents weight(g) of an intermediate phosphoric ester which is produced in the first step, B represents content(%) of chlorine in the intermediate phosphoric ester, C represents molecular weight of the alkylene oxide and 35.5 is atomic weight of chlorine, to 10 wt % excess thereof.

18. The process according to claim 17, wherein the alkylene oxide is used in an amount within the range from 2 to 6 wt % excess thereof.

19. The process according to claim 1, wherein the reaction of the second reaction mixture with alkylene oxide is conducted at a temperature within a range from about 40° to about 110° C.

20. The process according to claim 1, wherein the reaction of the second reaction mixture with alkylene oxide is conducted in the presence of a Lewis acid catalyst.

21. The process according to claim 20, wherein the Lewis acid catalyst is selected from the group consisting of titanium tetrachloride and magnesium oxide.

22. The process according to claim 21, wherein the Lewis acid catalyst is titanium tetrachloride, which is added in an amount of 2.3 to 23.0 millimoles with respect to 1 mole of the intermediate phosphoric ester.

23. The process according to claim 22, wherein the Lewis acid catalyst is titanium tetrachloride, which is added in an amount of 2.3 to 11.5 millimoles with respect to 1 mole of the intermediate phosphoric ester.

24. The process according to claim 1, wherein the tribromoneopentyl chloroalkyl phosphate contains 5 wt % or less phosphoric ester represented by the formula (2):

wherein R represents a hydrogen atom, or an alkyl or chloroalkyl group.

* * * * *